(12) United States Patent
Lee et al.

(10) Patent No.: US 11,550,145 B2
(45) Date of Patent: Jan. 10, 2023

(54) OPTICAL SYSTEM FOR IMPLEMENTING AUGMENTED REALITY AND DEVICE INCLUDING THE SAME

(71) Applicant: KOREA PHOTONICS TECHNOLOGY INSTITUTE, Gwangju (KR)

(72) Inventors: Kwanghoon Lee, Anyang-si (KR); Dongkil Lee, Gwangju (KR); Sungguk Chun, Gwangju (KR); Sungjoon Kim, Gwangju (KR); Seonkyu Yoon, Gwangju (KR)

(*) Notice: Subject to any disclaimer, the term of this patent is extended or adjusted under 35 U.S.C. 154(b) by 0 days.

(21) Appl. No.: 16/719,960

(22) Filed: Dec. 18, 2019

(65) Prior Publication Data

US 2020/0225464 A1    Jul. 16, 2020

(30) Foreign Application Priority Data

Jan. 16, 2019   (KR) .................. 10-2019-0005724
Mar. 19, 2019   (KR) .................. 10-2019-0030952
Mar. 19, 2019   (KR) .................. 10-2019-0030971

(51) Int. Cl.
*G02B 26/08*   (2006.01)
*G02B 27/10*   (2006.01)
(Continued)

(52) U.S. Cl.
CPC ..... *G02B 26/0833* (2013.01); *G02B 27/1033* (2013.01); *G06T 19/006* (2013.01); *H04N 5/238* (2013.01); *H04N 5/332* (2013.01)

(58) Field of Classification Search
CPC ............ G02B 26/0833; G02B 27/1033; G06T 19/006; H04N 5/332; H04N 5/238
See application file for complete search history.

(56) References Cited

U.S. PATENT DOCUMENTS 5,969,754 A * 10/1999 Zeman ................. H04N 5/2256
                                                           348/136
2012/0007839 A1 * 1/2012 Tsao ...................... G06T 19/006
                                                           345/204

FOREIGN PATENT DOCUMENTS

EP        2544039 A1      1/2013
JP        1985-069614     4/1985
(Continued)

OTHER PUBLICATIONS

English Specification of 1995-325266.
(Continued)

*Primary Examiner* — Wing H Chow
(74) *Attorney, Agent, or Firm* — Antonio Ha & U.S. Patent, LLC

(57) ABSTRACT

An augmented reality optical device includes an image generator receiving a preset wavelength range of light reflected by an affected part and generating an affected part image, an image output unit outputting a visible wavelength range of light corresponding to the affected part image, a first mirror unit reflecting the light output from the image output unit, a lens unit focusing the reflected light, a beam splitter reflecting a preset wavelength range of light incident from the outside in a preset direction and transmitting a portion of an incident visible wavelength range of light to a user's pupil (or in the preset direction) while reflecting another portion of the incident visible wavelength range of light in the preset direction (or to the user's pupil), and a second mirror unit re-reflecting the preset wavelength range of light reflected by the beam splitter to the image generator.

4 Claims, 18 Drawing Sheets

(51) Int. Cl.
*G06T 19/00* (2011.01)
*H04N 5/238* (2006.01)
*H04N 5/33* (2006.01)

(56) References Cited

FOREIGN PATENT DOCUMENTS

| | | |
|---|---|---|
| JP | S60-69614 | 4/1985 |
| JP | H06-319765 | 11/1994 |
| JP | 1995-325266 | 12/1995 |
| JP | H07-325266 | 12/1995 |
| JP | 2001-211403 A | 8/2001 |
| JP | 2008-018015 A | 1/2008 |
| KR | 2015-529482 A | 10/2015 |
| KR | 10-2017-0020186 | 2/2017 |
| KR | 10-2018-0136219 | 12/2018 |
| WO | WO2004-068197 | 8/2004 |

OTHER PUBLICATIONS

English Specification of 1985-069614.
English Specification of JP2008-018015A.
English Specification of 10-2017-0020186.
English Specification of EP2544039A1.
English Specification of JP2015-529482A.
English Specification of 10-2018-0136219.
English Specification of JPH07-325266.
English Specification of JPS60-69614.
English Specification of JP2001-211403A.
English Specification of WO2004-068197.

\* cited by examiner

OPTICAL SYSTEM FOR IMPLEMENTING AUGMENTED REALITY AND DEVICE INCLUDING THE SAME

CROSS-REFERENCE TO RELATED APPLICATION(S)

This application is based on and claims priority under 35 U.S.C. 119 to Korean Patent Application Nos. 10-2019-0005724, filed on Jan. 16, 2019, 10-2019-0030952, filed on Mar. 19, 2019, and 10-2019-0030971, filed on Mar. 19, 2019, in the Korean Intellectual Property Office, the disclosures of which are herein incorporated by reference in their entireties.

TECHNICAL FIELD

Embodiments of the disclosure relate to optical systems for implementing augmented reality and devices including the same.

DESCRIPTION OF RELATED ART

The description of the Discussion of Related Art section merely provides information that may be relevant to embodiments of the disclosure but should not be appreciated as necessarily constituting the prior art.

FIG. 1 is a view illustrating a configuration of an augmented reality optical device according to the prior art. Referring to FIG. 1, the conventional glasses-type augmented reality optical device 100 includes an image output unit 110, a lens unit 120, a beam splitter 130, and a mirror lens unit 140.

The image output unit 110 radiates light corresponding to an image to be output.

The lens unit 120 first collects light beams radiated from the front of the image output unit 110. The lens unit 120 prevents light beams from the image output unit 110 from spreading while collecting a sufficient amount of light onto the beam splitter 130.

The light beams passing through the lens unit 120 are reflected and second collected by the mirror lens unit 140 and are then re-reflected to the user's eyes by the beam splitter 130. The light beams reflected by the mirror lens unit 140 are collimated and incident onto the user's pupil 160. The light beams incident onto the user's pupil pass through the optics of the eye, forming an image on the retina which is perceived by the user. The user recognizes an AR image by viewing the actual image beyond the beam splitter, along with the image output from the image output unit 110.

The conventional glasses-type augmented reality optical device has the following inconveniences.

According to the conventional augmented reality optical device, collimated light is incident onto the retina at a very small angle and, resultantly, a very narrow angle of view (AOV) 160 is provided to the user. Thus, the AR image is provided in a very narrow area, and the sense of presence is deteriorated. To enhance the sense of presence, the AOV of AR image needs to be increased. This may be achieved by enlarging each component, e.g., the image output unit 110, lens unit 120, beam splitter 130, and mirror lens unit 140. This, however, results in the overall augmented reality optical device being bulky and uncomfortable to wear.

The AR image provided to the user may cause optical aberrations depending on the configuration and features of the optical system, which may deteriorate image quality. To prevent this, there should be no optical path difference between the light beams incident onto the retina—i.e., the optical system is required to have the nature of an ideal paraxial lens. However, this is impossible to achieve since every optical system has a real thickness. Optical aberrations are inevitable in all optical systems and resultant image deterioration is impossible to completely remove. Deterioration of light quality may occur depending on the positions and alignment of optical systems. Thus, how to configure the optical systems and deal with the housing is a critical issue. In the conventional augmented reality optical device, the lens unit 120 and the beam splitter 130 are separated from each other. It is very hard to place the lens unit 120 and the beam splitter 130 in precise positions and leave them motionless. Due to the foregoing issues, the conventional augmented reality optical device cannot deliver a better light quality of AR image to the user.

Meanwhile, doctors do surgery while checking the lesion with the naked eye. To that end, the border between the affected part and its surrounding tissues or normal tissues should be first identified precisely. In doing so, surgeons tend to rely merely on their eyes and touch. Despite analysis of image data obtained by various pieces of equipment, e.g., X-ray, CT, or PET, it is still tricky to figure out the border between the affected part and the normal tissues from live, moving human organs Because of this, a conventional way for surgery is to cut out a larger area expected to include the affected part. This way, however, leaves the problem that normal tissues, as well as the affected part, are cut out, resulting in a depression of the organ associated with the cut-out portion and hence a long period of time for rehabilitation.

An approach to address such issues is use of minimally invasive surgery (MIS) by which a surgeon proceeds with surgery while checking if the implant and surgery tool are inserted in a desired direction and position by steadily running a C-arm (portable X-ray). However, this may put the operating surgeon and staff to harmful X-ray exposure.

A more advanced method is that the operating surgeon performs surgery while viewing 3D CT images on the monitor. However, the need for frequent check on 3D CT images may hamper the operation process.

Thus, there are ongoing attempts to adopt AR technology for medical devices.

SUMMARY

An object of the disclosure is to provide an augmented reality optical device which may provide the user with images with a wide AOV and minimized optical aberration in a simplified configuration and an AR device including the augmented reality optical device.

Another object of the disclosure is to provide an optical system for implementing augmented reality that allows the user to recognize the affected part image or affected part information image along with the actual affected part of the patient via augmented reality by providing the user with the patient's affected part image or information image for the affected part using AR technology and a medical AR device including the optical system.

Another object of the disclosure is to provide an optical system for implementing augmented reality, which has a simplified configuration to allow the user to recognize the AR image along with the actual affected part and a medical AR device including the optical system.

Another object of the disclosure is to provide a beam splitter for implementing augmented reality that allows the user to recognize the affected part image or affected part information image along with the actual affected part of the patient via augmented reality by providing the user with the patient's affected part image or information image for the affected part using AR technology and an AR optical system including the beam splitter.

Another object of the disclosure is to provide a beam splitter for implementing augmented reality, which has a simplified configuration to allow the user to recognize the AR image along with the actual affected part and an AR optical system including the beam splitter.

According to an embodiment, an augmented reality optical device includes an image generator receiving a preset wavelength range of light reflected by an affected part and generating an image of the affected part, an image output unit outputting a visible wavelength range of light corresponding to the image generated by the image generator, a first mirror unit reflecting the light output from the image output unit, a lens unit focusing the light reflected by the first mirror unit, a beam splitter reflecting a preset wavelength range of light incident from an outside of the augmented reality optical device in a preset direction and transmitting a portion of an incident visible wavelength range of light to a user's pupil while reflecting another portion of the incident visible wavelength range of light in the preset direction or transmitting the portion of the incident visible wavelength range of light in the preset direction while reflecting the other portion of the incident visible wavelength range of light to the user's pupil, and a second mirror unit re-reflecting the preset wavelength range of light reflected by the beam splitter to the image generator.

The preset wavelength range of light may be an infrared or ultraviolet wavelength range of light.

The image output unit may receive, from the outside, an AR image to be output and outputs another visible wavelength range of light corresponding to the AR image.

The beam splitter may transmit a portion of the visible wavelength range of light incident from the outside to the user's pupil while reflecting another portion of the visible wavelength range of light in the preset direction.

The beam splitter may reflect a portion of the visible wavelength range of light reflected by the first mirror unit to the user's pupil while transmitting another portion of the visible wavelength range of light in the preset direction.

The beam splitter may include a reflection surface reflecting the preset wavelength range of light and another reflection surface reflecting or transmitting the visible wavelength range of light.

According to an embodiment, an augmented reality optical device includes an image generator receiving a preset wavelength range of light reflected by an affected part and generating an image of the affected part, an image output unit outputting a visible wavelength range of light corresponding to the image generated by the image generator, a lens unit focusing the light output from the image output unit, a beam splitter reflecting a preset wavelength range of light incident from an outside of the augmented reality optical device in a preset direction and transmitting a portion of an incident visible wavelength range of light to a user's pupil while reflecting another portion of the incident visible wavelength range of light in the preset direction or transmitting the portion of the incident visible wavelength range of light in the preset direction while reflecting the other portion of the incident visible wavelength range of light to the user's pupil, and a mirror unit re-reflecting the preset wavelength range of light reflected by the beam splitter to the image generator.

The preset wavelength range of light may be an infrared or ultraviolet wavelength range of light.

The image output unit may receive, from the outside, an AR image to be output and outputs another visible wavelength range of light corresponding to the AR image.

The beam splitter may transmit a portion of the visible wavelength range of light incident from the outside to the user's pupil while reflecting another portion of the visible wavelength range of light in the preset direction.

The beam splitter may reflect a portion of the visible wavelength range of light transmitted through the lens unit to the user's pupil while transmitting another portion of the visible wavelength range of light in the preset direction.

The beam splitter may include a reflection surface reflecting the preset wavelength range of light and another reflection surface reflecting or transmitting the visible wavelength range of light.

According to an embodiment, a medical augmented reality device includes an image generator receiving a preset wavelength range of light reflected by an affected part and generating an image of the affected part, an image output unit outputting a visible wavelength range of light corresponding to the image generated by the image generator, an augmented reality optical device, a controller controlling the image generator, the image output unit, and the augmented reality optical device, and a power supply supplying power to the image generator, the image output unit, the augmented reality optical device, and the controller.

As described above, an embodiment of the disclosure may provide the user with images with a wide AOV and minimized optical aberration.

According to an embodiment, an augmented reality optical device may be implemented in a compact, simplified configuration, with a wide AOV and minimized aberration.

According to an embodiment, an augmented reality optical device may adopt AR technology to provide an affected part image for the patient or an information image for the affected part to the user. Thus, the user may identify the affected part image or affected part information image, along with the patient's actual affected part without the need for frequently checking on a separate monitor output screen, e.g., during surgery.

According to an embodiment, the augmented reality optical device has a compact, simplified configuration which may be easily worn on the user.

BRIEF DESCRIPTION OF THE DRAWINGS

A more complete appreciation of the disclosure and many of the attendant aspects thereof will be readily obtained as the same becomes better understood by reference to the following detailed description when considered in connection with the accompanying drawings, wherein.

DETAILED DESCRIPTION OF EXEMPLARY EMBODIMENTS

Various changes may be made to the disclosure, and the disclosure may come with a diversity of embodiments. Some embodiments of the disclosure are shown and described in connection with the drawings. However, it should be appreciated that the disclosure is not limited to the embodiments, and all changes and/or equivalents or replacements thereto also belong to the scope of the disclosure. Similar reference denotations are used to refer to similar elements throughout the drawings.

The terms "first" and "second" may be used to describe various components, but the components should not be limited by the terms. The terms are used to distinguish one component from another. For example, a first component may be denoted a second component, and vice versa without departing from the scope of the disclosure. The term "and/or" may denote a combination(s) of a plurality of related items as listed or any of the items.

It will be understood that when an element or layer is referred to as being "on," "connected to," "coupled to," or "adjacent to" another element or layer, it can be directly on, connected, coupled, or adjacent to the other element or layer, or intervening elements or layers may be present. In contrast, when a component is "directly connected to" or "directly coupled to" another component, no other intervening components may intervene therebetween.

The terms as used herein are provided merely to describe some embodiments thereof, but not to limit the disclosure. As used herein, the singular forms "a," "an," and "the" are intended to include the plural forms as well, unless the context clearly indicates otherwise. As used herein, the term "comprise," "include," or "have" should be appreciated not to preclude the presence or addability of features, numbers, steps, operations, components, parts, or combinations thereof as set forth herein.

Unless otherwise defined, all terms including technical and scientific terms used herein have the same meaning as commonly understood by one of ordinary skill in the art to which the embodiments of the disclosure belong.

It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The components, processes, steps, or methods according to embodiments of the disclosure may be shared as long as they do not technically conflict with each other.

Figure 1:
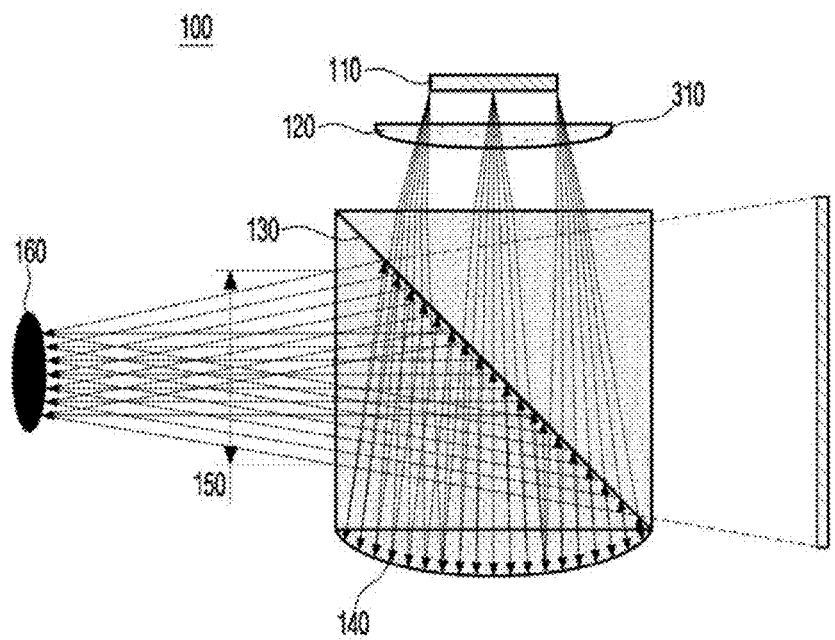
FIG. 1 is a view illustrating a configuration of an augmented reality optical device according to the prior art.
Figure 2:
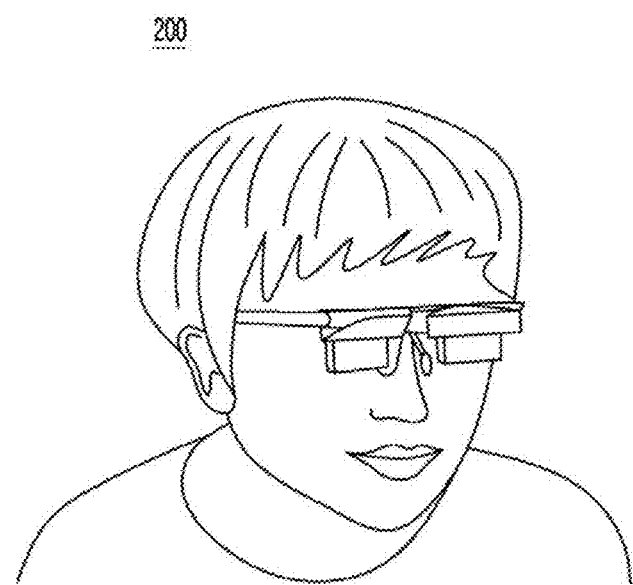
FIG. 2 is a view illustrating an example augmented reality device according to an embodiment.
Figure 3:
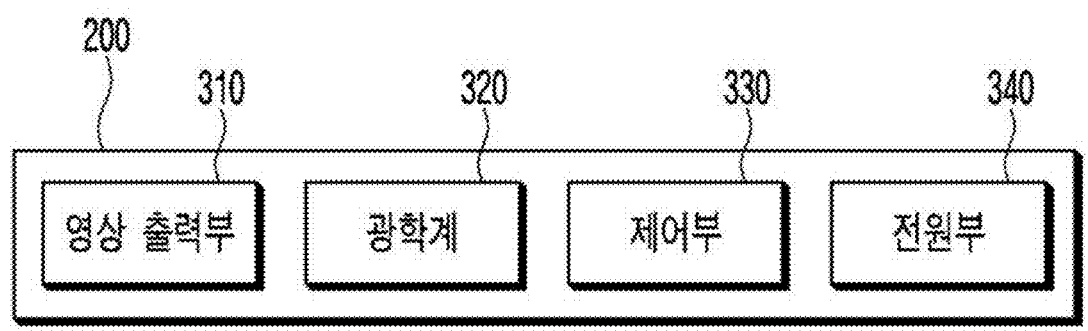
FIG. 3 is a block diagram illustrating a configuration of an augmented reality device according to an embodiment.

FIG. 2 is a view illustrating an example augmented reality device according to an embodiment. FIG. 3 is a block diagram illustrating a configuration of an augmented reality device according to an embodiment.

Referring to FIGS. 2 and 3, according to an embodiment of the disclosure, an augmented reality (AR) device 200 includes an image output unit 310, an optical system 320, a controller 330, and a power unit 340.

The augmented reality device 200 is worn on the user, or without being worn, providing augmented reality images to the user. The user may perceive augmented reality by viewing both the actual environment image which is viewable by the augmented reality device 200 and the augmented reality image provided from the augmented reality device 200.

The image output unit 310 outputs light corresponding to an augmented reality image. The image output unit 310 may be connected with an external source via, e.g., a cable or universal serial bus (USB), to receive the image, or the image output unit 310 may wirelessly receive the image via a separate communication unit (not shown). The image output unit 310 outputs light corresponding to the received image so that the user may view the augmented reality image. The image output unit 310 may be, or include, at least one of various types of displays including, but not limited to, optical projectors, liquid crystal displays (LCDs) or organic light emitting diode (OLED) displays, as conventionally used in AR devices.

The augmented reality optical system 320 (hereinafter, simply referred to as an "optical system") transfers the light (image) output from the image output unit 310 to the user. The optical system 320 is configured to provide images with a wide angle of view (AOV) and minimized optical aberrations. The user may view wide-AOV augmented reality images which are clear, crisp, and distortion-free. The optical system 320 is described below in greater detail with reference to FIG. 4.

The controller 330 controls the operation of the components 310, 320, and 340. The controller 330 may receive operation control signals for the components (e.g., to turn on or off the AR device 200) from the user of the AR device 200 and control the components to operate according to the operation control signals.

The power unit 340 provides power to the components 310 to 330 to operate the components 310 to 330.

Figure 4:
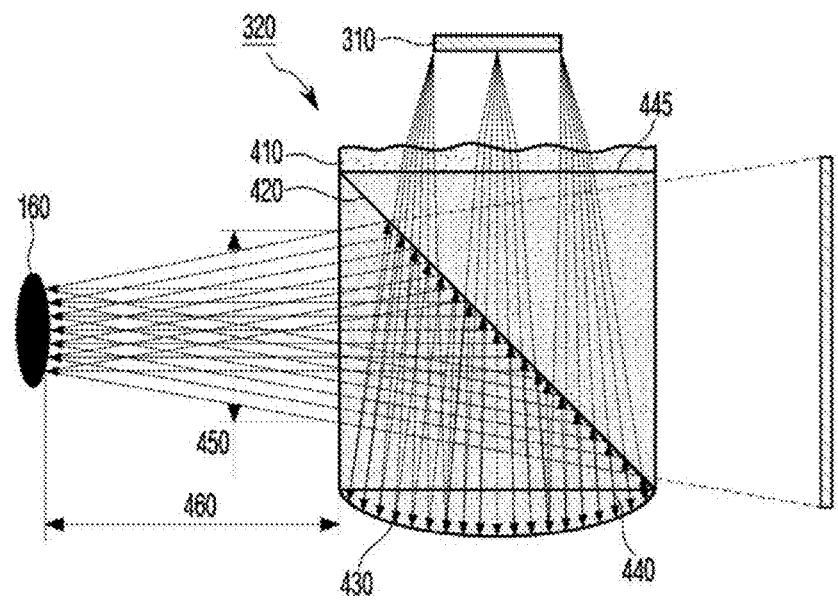
FIG. 4 is a view illustrating a configuration of an augmented reality optical system according to an embodiment.

FIG. 4 is a view illustrating a configuration of an augmented reality optical system according to an embodiment.

Referring to FIG. 4, according to an embodiment of the disclosure, the optical system 320 includes a lens 410, a beam splitter 420, and a mirror lens unit 430.

The lens 410 is formed of a material with a predetermined refractive index. The lens 410 may contact the beam splitter 420 to collect or focus light radiated from the image output unit 310.

The lens 410 may be formed of a material with a refractive index different from those of the beam splitter 420 and the mirror lens unit 430. The lens 410 may be formed of a material with a larger refractive index than the materials of the beam splitter 420 and the mirror lens unit 430. When the optical system 320 is constituted of media with different refractive indexes, it is possible to easily control chromatic aberration which results in different focal lengths depending on wavelength ranges. Even without adding a separate component, or modifying the existing configuration, to minimize chromatic aberration, the optical system 320 may get rid of chromatic aberration in a simple and effective manner by including the lens 410 formed of a material with a refractive index different from (e.g., larger than) the beam splitter 420 and the mirror lens unit 430.

The lens 410 may contact the beam splitter 420 to collect or focus the light radiated from the image output unit 310. The lens 410 may have a non-spherical shape to focus beams differently depending on the positions where the light beams are incident, rather than focusing the light beams onto the same point. The lens 410 may refract the light minimally in the center thereof and refract more as getting away from the center. If the lens is spherical as in the prior art, spherical aberration occurs so that the light beams striking the spherical surface off-center may not travel along an optical path of an ideal lens (hereinafter, such an optical path is referred to as an "ideal optical path") but rather go along an optical path which may cause light beams to be focused insufficiently or excessively. Thus, if a spherical lens is used, an additional lens or medium is required or the lens needs to be thick enough to allow light beams striking the spherical surface in various positions, particularly light beams striking the surface off-center, to be focused as close to the ideal optical path as possible. For example, in the conventional optical system, the spherical lens is placed apart from the beam splitter so that light beams passing through the spherical lens are first refracted by the air which is a different medium than the spherical lens and are incident on, and secondly refracted by, the beam splitter which is formed of a different medium from the air. As described above, if the spherical lens and the beam splitter are spaced apart from each other, since the refractive power of the spherical lens is even over the entire lens surface, only paraxial ray conditions may be aberration-controlled. Thus, if the AOV is increased, a significant optical aberration and image distortion may occur, and it is difficult to implement clear, distortion-free AR images. Further, it is not easy to precisely align the lens and the beams splitter along the optical axis. Thus, in the optical system with the optical components spaced apart from each other, it is very hard to prevent any one of the components from moving off its position. Further, the space required for configuring the optical system inevitably increases the overall volume of the optical system. As another example, for light beams striking the lens surface off-center to be sufficiently focused onto the beam splitter, the refractive index of the lens needs to increase, with the result of the need for use of a bulky and thick lens. To secure a volume for such a thick lens, the lens ends up being disposed a predetermined distance apart from the beam splitter. To provide the user with clear, distortion-free AR images, the lens or beam splitter needs to be finely adjusted to be disposed in the precise position and, after positioned, should not be moved. The optical system 320 includes the lens 410 which is non-spherical and may deliver a sufficient refractive power for increasing AOV. The lens 410 contacts, and is integrally formed with, the beam splitter 420.

Thus, the optical system 320 enables easier implementation of the optical performance as originally designed, is free from any alignment issues and, although small in volume, it may implement images of a wide AOV. In other words, unlike in the conventional optical system, although no medium (e.g., air or a separate additional component) with a different refractive index is added between the lens and the beam splitter as in the conventional optical system, the optical system 320 may implement clear, distortion-free AR images.

The beam splitter 420 transmits light beams which have passed through the lens 410 and re-reflects light beams reflected by the mirror lens unit 430. One surface of the beam splitter 420 contacts the lens 410, and another surface of the beam splitter 420 contacts the mirror lens unit 430. The beam splitter 420 transmits light beams which pass through the lens 410 (in the −y axis direction) and re-reflects light beams which have been reflected (in the +y axis direction) by the mirror lens unit 430 towards the user's pupil 160 (in the −x axis direction).

The mirror lens unit 430 re-reflects the light beams passing through the beam splitter 420 to the beam splitter 420.

The mirror lens unit 430 is formed of a material with the same refractive index as the beam splitter 420. Thus, the light beams passing through the beam splitter 420 to the mirror lens unit 430 and the light beams reflected by the mirror lens unit 430 to the beam splitter 420 undergo no change in path or no increase or decrease in aberration. As described above, as the mirror lens unit 430 and the beam splitter 420 are formed of materials with a lower refractive index than the lens 410, the chromatic aberration of light beams incident onto the beam splitter 420 or mirror lens unit 430 is controlled.

The mirror lens unit 430 is implemented to be non-spherical, reflecting incident light beams at different angles depending on the positions where the light beams are incident. If the mirror lens unit is implemented to be spherical as in the conventional optical system, incident light beams focused by the lens are reflected evenly depending on the positions where the light beams are incident. Thus, not all of the light beams output from the image output unit are incident onto the user's pupils, or the chromatic aberration of the light beams passing through the mirror lens unit 430 and the beam splitter 420 may increase. In contrast, the mirror lens unit 430 is implemented to be non-spherical, all of the focused light beams may be incident onto the pupil 160 and the reflected light beams are formed so that collimated light beams are incident onto the surface of the pupil 160. Light beams are reflected at larger angles on the off-center portion of the mirror lens unit 430 off-center than on the center portion of the mirror lens unit 430, so that all of the light beams reflected by the mirror lens unit 430 and re-reflected by the beam splitter 420 are incident onto the pupil 160. The mirror lens unit 430 is implemented to have a non-spherical surface with a preset coefficient different from the non-spherical coefficient of the lens 410 so that collimated light beams are incident onto the pupil 160. Since the light beams reflected by the mirror lens unit 430 and the beam splitter 420 are incident, as collimated light beams, to the surface of the pupil 160, the user may perceive as if AR image information is coming in from infinite positions, and the perceived AR image has a screen size corresponding to the given AOV range and the image quality of being very deep and clear.

Both the mirror lens unit 430 and the lens 410 are implemented to be non-spherical, and the optical aberrations of light beams (AR images) incident onto the pupil 160 may be minimized by adjusting each of the non-spherical coefficients of the components 410 and 430. As the lens 410 and the mirror lens unit 430 have different non-spherical coefficients, aberrations may be suppressed. Optical aberrations which may occur include chromatic aberration, coma, astigmatism, curvature of field, and distortion. The optical system 320 includes the mirror lens unit 430 and the lens 410 which are implemented to be non-spherical and to have preset non-spherical coefficients, thus minimizing optical aberrations simply even without a separate, additional component.

The lens 410 is implemented to be non-spherical and has significantly increased resolving power as compared with conventional spherical lenses, thus significantly increasing the resolution for the AOV of AR images provided to the user. Since the lens 410 has a non-spherical shape, spherical aberration may be minimized and, even for light beams incident onto the off-center portion of the lens 410, errors from the ideal optical path may be minimized. In other words, since light beams, no matter what positions of the lens 410 they are incident, have as close paths to the ideal optical path as possible, the user may separately recognize light beams radiated from the pixels of the image output unit. Thus, the lens 410 increases the resolution of the AR image provided to the user. Further, the mirror lens unit 430 may also be implemented to be non-spherical. The mirror lens unit 430, like the lens 410, may minimize the error or difference between the path of light incident onto the mirror lens unit 430 and the ideal optical path. The optical system 320 includes the lens 410 which is non-spherical or includes the lens 410 and the mirror lens unit 430 which are both non-spherical, thus properly focusing light beams incident onto the off-center portion of the lens 410 as well as light beams incident onto the portion near the optical axis to have the ideal optical path (i.e., not to be focused excessively or insufficiently) and hence providing wide-AOV, distortion-free images to the user.

One side of the beam splitter 420 contacts the lens 410, and another side of the beam splitter 420 contacts the mirror lens unit 430. Adhesive media 440 and 445 are used to fix the components 410 and 430 to the beam splitter 420. The adhesive medium 440 that allows the beam splitter 420 and the mirror lens unit 430 to contact and be fixed to each other has the same refractive index as the beam splitter 420 and the mirror lens unit 430. The optical properties which need to be finely adjusted for ensuring an AOV and suppressing aberrations may be varied by the adhesive medium 440. To prevent this, the adhesive medium 440 is formed of a material with the same refractive index as the beam splitter 420 and the mirror lens unit 430. In contrast, the adhesive medium 445 that allows the lens 410 and the beam splitter 420 to contact and be fixed to each other is formed of a semi-transmissive medium or material that may transmit or reflect light beams incident onto the beam splitter 420, with the transmission and reflection adjustable in a predetermined ratio. In this case, optical properties, such as optical path, may be varied by the optical nature of the adhesive medium 445. To prevent this, the adhesive medium 445 may have a preset thickness to compensate for the varying optical property. The adhesive medium 445 has a preset thickness and attaches the components 410 and 420 together, thereby minimizing variations in the optical properties by its own.

Since the optical system 320 allows light beams to be incident onto the pupil 160 in the form of straight lines as collimated light, the distance 460 between the pupil 160 and the optical system 320 need not be short. Since the incident angle of the collimated light to the pupil is proportional to the AOV of the optical system, the repositioning of the pupil, i.e., range of rotation of the eyeball, may be sufficiently met, allowing for more user immersion and a wide AOV and high presence. The conventional optical system provides AR images of a narrow AOV due to influence by the above-described configuration and optical properties limited by the configuration, failing to deliver user immersion and high presence. According to an embodiment, the optical system 320 allows light beams to be incident onto the pupil 160 in the form of straight lines, as collimated light, so that the position of the pupil 160 is not limited to the focal length. Thus, although the optical system may not be positioned sufficiently close to the user, e.g., the user wearing glasses or the augmented reality device 200 being not of a wearable type, the optical system 320 allows the user to easily view AR images.

Figure 5:
FIG. 5 is a view illustrating a screen output from an augmented reality optical system according to an embodiment.

FIG. 5 is a view illustrating a screen output from an augmented reality optical system according to an embodiment. FIG. 5 illustrates an actual output screen when the augmented reality device 200 is implemented as a glasses-type HMD device which is worn on the user. Referring to FIG. 5, the augmented reality device 200 may deliver aberration-controlled, clear screens and provide the user with high-resolution (e.g., full HD) AR images. This is the nature of the non-spherical optical system, representing that the optical system 320 has a lens resolving power capable of sufficiently displaying 0.7-inch full HD images.

Figure 6:
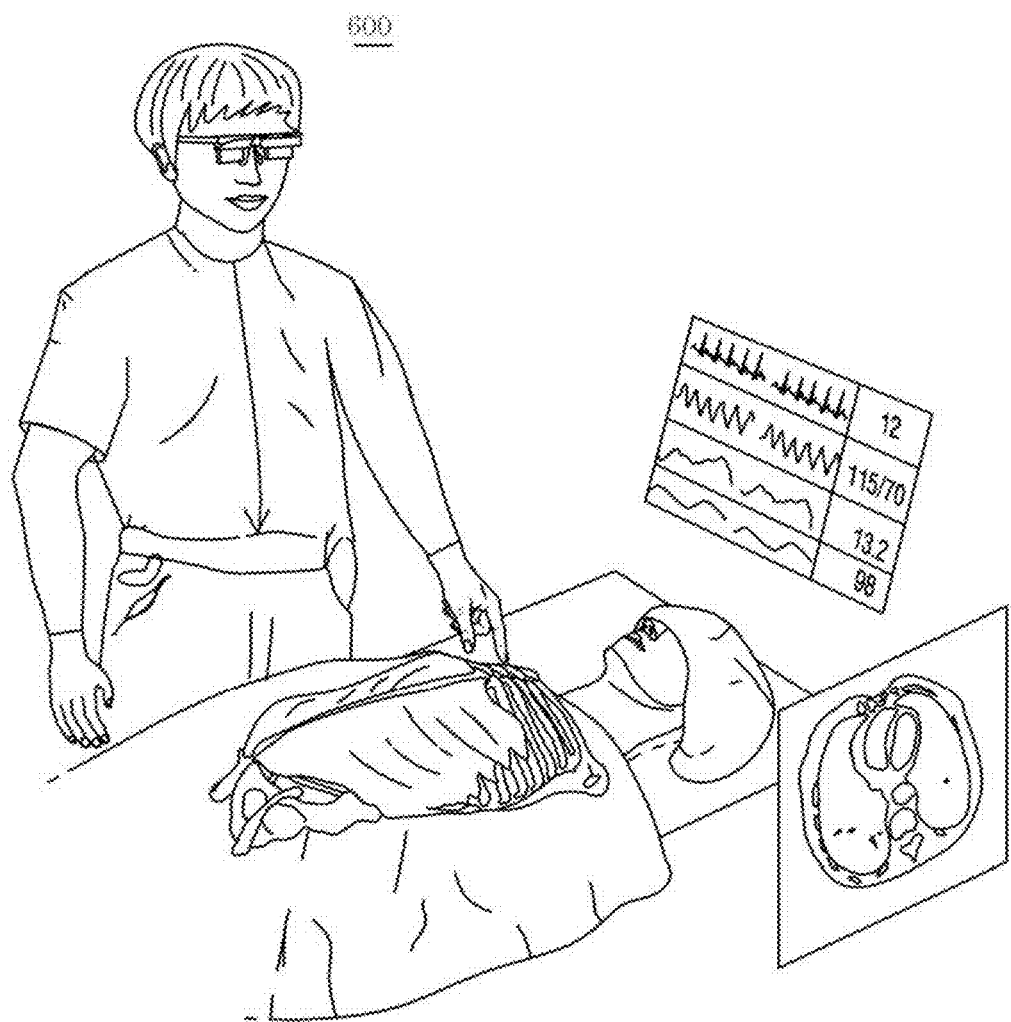
FIG. 6 is a view illustrating an example of a medical augmented reality device according to an embodiment.
Figure 7:
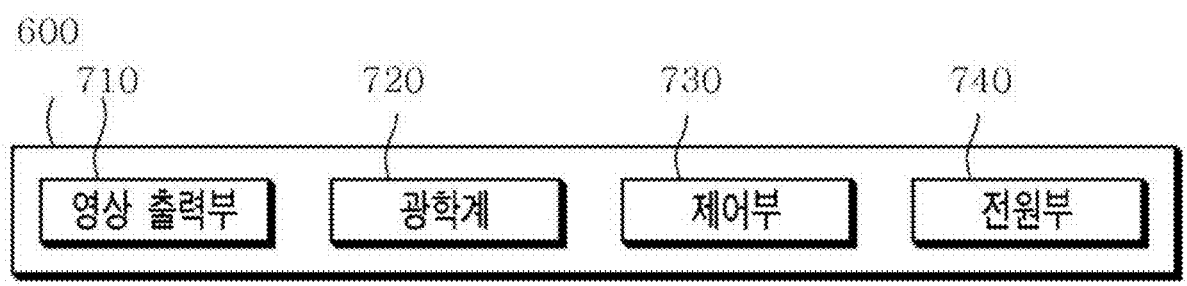
FIG. 7 is a view illustrating a configuration of a medical augmented reality device according to an embodiment.

FIG. 6 is a view illustrating an example medical augmented reality device according to an embodiment. FIG. 7 is a block diagram illustrating a configuration of a medical augmented reality device according to an embodiment.

The medical augmented reality device 600 is worn on the user (e.g., a doctor), or without being worn, providing augmented reality images to the user. AR images that the medical augmented reality device 600 provides include an affected part image which is an image only for the affected part and an affected part information image including information regarding the affected part. The user may view the AR image provided by the medical augmented reality device 600 and the actual image of the affected part which may be viewed beyond the medical augmented reality device 600. Thus, the user may simultaneously view the AR image, such as the affected part image, and the actual image of the affected part, which rids the user of inconvenience of turning his head to identify the AR image.

The affected part image may be generated as follows. If the patient drinks a reagent containing a material which emits light only in a preset wavelength range or has the reagent applied around the affected part, the affected part reflects the preset wavelength range of light. When the preset wavelength range of light is radiated to the affected part, the affected part generates or reflects the wavelength range of light by the material. By using such nature, the medical augmented reality device 600 receives the preset wavelength range of light and generates an image for the affected part, thereby generating the affected part image. The preset wavelength range may be a wavelength range invisible to the user, e.g., infrared or ultraviolet wavelength range, other than the visible light wavelength range.

The affected part information image includes the following images. The affected part information image includes an image obtained by capturing the affected part by X-ray, CT, or MRI, or a basic medical image indicating the patient's condition, e.g., heartrate.

Referring to FIG. 7, according to an embodiment of the disclosure, a medical augmented reality (AR) device 600 includes an image output unit 710, an optical system 720, a controller 730, and a power unit 740.

The image output unit 710 outputs light corresponding to an augmented reality image. The image output unit 710 receives an AR image (e.g., affected part image) generated by the optical system 720 and outputs light corresponding to the augmented reality image. The image output unit 710 receives an AR image (e.g., affected part information image) from the outside via a wired connection to the outside or universal serial bus (USB) or via a separate communication unit (not shown) and outputs light corresponding to the received AR image. The image output unit 710 outputs a visible light wavelength range of light so that the user may view the AR image. The image output unit 310 may be, or include, at least one of various types of displays including, but not limited to, optical projectors, liquid crystal displays (LCDs) or organic light emitting diode (OLED) displays, as conventionally used in AR devices.

The augmented reality optical system 720 (hereinafter, simply referred to as an "optical system") transfers the light corresponding to the actual image of the affected part and the light (image) output from the image output unit 710. The optical system transfers the light corresponding to the actual image of the affected part incident from the patient's affected part to the user, thereby allowing the user to view the patient's affected part. Further, the optical system 720 generates an affected part image from a preset wavelength range of light incident to the optical system 720 and transfers the affected part image generated and output from the image output unit 710 to the user. Thus, the user may simultaneously view the actual affected part and the affected part image in the position near the actual affected part and may perceive the affected part image as augmented reality. The user may simultaneously view the affected part and the affected part image without the need for turning his head to the monitor displaying the affected part image. The optical system 720 transfers the affected part information image output from the image output unit 710 to the user. In this case, the affected part information image is output near the actual affected part and the process information not to obstruct the user from viewing the actual affected part and affected part image. Thus, the optical system 720 transfers the affected part information image to the user in such a manner that the affected part information image is output a predetermined distance away from the actual affected part and the affected part image. For example, if the actual affected part and the affected part image are positioned in the center of the user's field of view, the affected part information image may be positioned off the center of the user's field of view. A configuration for the optical system 720 to transfer light corresponding to the AR image and the actual image of the affected part is described below in detail with reference to FIGS. 8 to 20.

The controller 730 controls the operation of the components 710 and 740. The controller 730 may receive operation control signals for the components (e.g., to turn on or off the AR device 600) from the user of the medical AR device 600 and control the components to operate according to the operation control signals.

The power unit 740 provides power to the components 710 to 730 to operate the components 710 to 730.

Figure 8A:
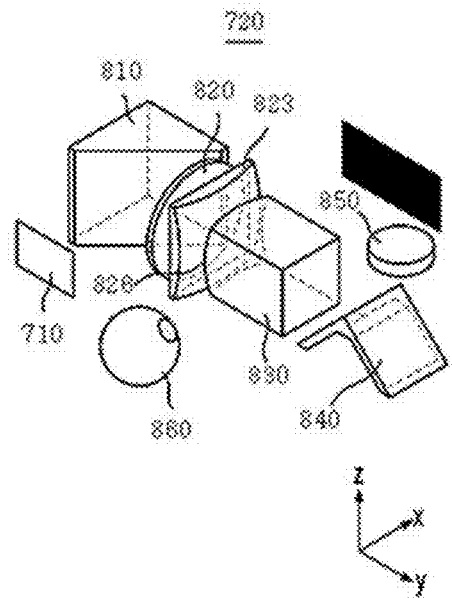
FIG. 8A is a perspective view illustrating an augmented reality optical device according to a first embodiment.
Figure 8B:
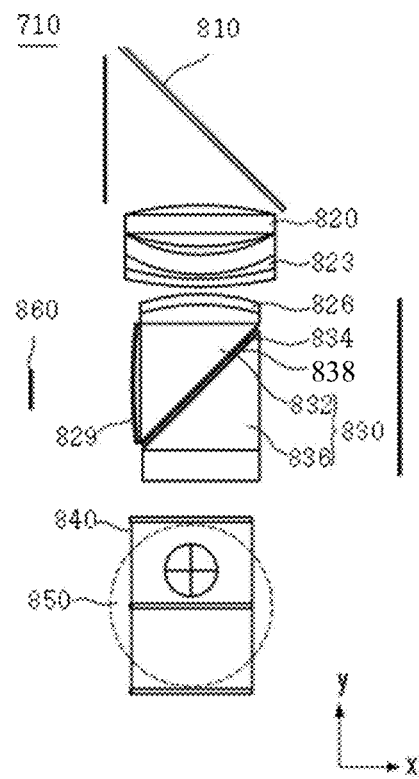
FIG. 8B is a plan view illustrating an augmented reality optical device according to the first embodiment.

FIG. 8A is a perspective view illustrating an augmented reality optical device according to a first embodiment. FIG. 8B is a plan view illustrating an augmented reality optical device according to the first embodiment.

Referring to FIGS. 8A and 8B, the optical system 720 of the first embodiment includes a first mirror unit 810, lens units 820, 823, 826, and 829, a beam splitter 830, a second mirror unit 840, and an image generator 850. Although FIG. 3 illustrates a configuration in which an image is incident to one pupil of the user for illustration purposes, another first mirror unit 810, other lens units 820, 823, 826, and 829, and another beam splitter 830 are arranged along the +y axis direction and symmetrically with respect to the second mirror unit 840.

The first mirror unit 810 reflects the light output from the image output unit 710 to the beam splitter 830. The first mirror unit 810 reflects the light corresponding to the AR image output from the image output unit 710 to the beam splitter 830 so that the light may be incident through the beam splitter 830 to the user's pupil 860.

The lens units 820, 823, 826, and 829 focus the light reflected by the first mirror unit 810 to the user's pupil 860. The lens units 820, 823, 826, and 829 are arranged on the path of the light reflected by the first mirror unit 810 to the user's pupil 860 and focuses the light to be incident, as collimated light, onto the user's pupil. Thus, the user may perceive as if the AR image is output from infinite positions and, thus, the AR image may have a screen size corresponding to a wide AOV range and deliver a deep and clear quality of image. The lens units 820, 823, and 826 are arranged between the first minor unit 810 and the beam splitter 830, focusing light and adjusting the optical path. The lens unit 829 is disposed between the beam splitter 830 and the user's pupil 860, focusing light and adjusting the optical path. As shown in FIGS. 8A and 8B, the lens units 820, 823, 826, and 829 may include a plurality of spherical lenses and one or a small number of non-spherical lenses.

The beam splitter 830 includes a plurality of components 832 and 836 with reflection surfaces 834 and 838 on the interfacial surfaces of the components 832 and 836 to thereby reflect all of light beams with a preset wavelength range while separating and reflecting or transmitting a visible light wavelength range of light.

The beam splitter 830 includes a first component 832 and a second component 836 which respectively have reflection surfaces 834 and 838 to reflect or transmit a specific wavelength range of light. The reflection surfaces 834 and 838 may be coated on the respective interfacial surfaces of the components 832 and 836, which face each other, and may then be bonded together. Alternatively, one of the reflection surfaces 834 and 838 may be coated on the interfacial surface of one of the components 832 and 836 and then the other reflection surface and the other component may be sequentially bonded thereto. As such, as the reflection surfaces 834 and 838 formed on the interfacial surfaces of the components 832 and 836 of the beam splitter 830 are bonded together without an air gap therebetween, the issue with a variation in the path of light incident onto the beam splitter 830 that would occur if an air gap is present may be removed, and unintentional total reflection that may occur at a certain incident angle of light incident onto the beam splitter 830 may be prevented.

The first reflection surface 834 separates a visible wavelength range of incident light beams and reflect some of the light beams while transmitting the others of the light beams. For example, the first reflection surface 834 may reflect a half of incident light beams of a visible wavelength range and transmit the other half. Thus, some of the light beams corresponding to the AR image, which are incident through the lens units 820, 823, and 826 to the beam splitter 830 are reflected by the first reflection surface 834 to the user's pupil 860, and the others are transmitted through the first reflection surface 834. Some of light beams corresponding to the actual image of the affected part incident from the outside (in the −x axis direction) are reflected by the first reflection surface 834 to the second mirror unit 840, and the others pass through the first reflection surface 834 to the user's pupil 860. The second reflection surface 838 reflects all of a preset wavelength range of light beams while transmitting the other wavelength ranges of light beams. The preset wavelength range of light, e.g., infrared or ultraviolet light, if incident onto the pupil, may negatively affect the eyeball. Thus, the preset wavelength range of light beams incident (in the −x axis direction) from the outside (e.g., a position in the +x axis with respect to the beam splitter in FIGS. 8A and 8B) are reflected by the second reflection surface 838 to the second mirror unit 840 while the light corresponding to the actual image of the affected part incident from the outside passes through the second reflection surface 838. By having such a structure, the beam splitter 830 may provide the user with both the actual image and AR image despite its minimized volume.

The second mirror unit 840 reflects the light reflected by, or transmitted through, the beam splitter 830 to the image generator 850. As shown in FIGS. 8A and 8B, the second mirror unit 840 reflects the preset wavelength range of light reflected by the beam splitter 830 or the visible wavelength range of light reflected by, or transmitted through, the beam splitter 830 to the image generator 850. The second mirror unit 840 may be shaped as a triangular prism with a bottom opening, and two opposite surfaces of the second mirror unit 840 which face the beam splitter 830 reflect light. Since the second mirror unit 840 reflect light beams coming from both beam splitters (e.g., the beam splitter 830 shown in FIG. 8A and another beam splitter (not shown) positioned opposite the beam splitter 830) to the image generator 850. Thus, one image generator 850 alone may receive light beams coming from both the beam splitters. As such, the optical system 720, although using only one image generator 850, is able to provide three-dimensional (3D) effects and depth of AR images to the user. The bottom opening of the second mirror unit 840 may provide enhanced wearability by preventing the augmented reality device with the optical system 720 from escaping off the user.

The image generator 850 is disposed over the second mirror unit 840 in a vertical direction (e.g., +Z axis), receiving the light reflected by the second mirror unit 840. The second mirror unit 840 reflects the light beams coming from both the beam splitters positioned on both sides of the second mirror unit 840 (along the y axis). Only one image generator 850 may be included in the optical system 720. The image generator 850 distinctly receives the light beams coming from one beam splitter and the light beams coming from the other beam splitter. The image generator 850 includes optical sensors (not shown) on both sides of the center thereof, which sense only a preset wavelength range of light. Since the preset wavelength range of light is used to generate an image but the visible wavelength range of light is not, the image generator 850 includes the optical sensors (not shown) sensing the preset wavelength range of light. The image generator 850 senses the preset wavelength range of light coming in two directions by the two optical sensors and generates an affected part image using the sensed information. The image generator 850 generates the affected part image and transfers the affected part image to each image output unit 710. Each image output unit 710 outputs light corresponding to the generated affected part image.

Since the optical system 720 includes only one image generator 850 to handle a plurality of light beams although the plurality of light beams are incident onto different positions to be recognized by the user's eyes, the overall size or volume of the optical system 720 may advantageously be reduced. The preset wavelength range may be an infrared (IR) or ultraviolet (UV) wavelength range. The image generator 850 may be implemented as an IR or UV camera, but embodiments of the disclosure are not limited thereto.

Figure 9A:
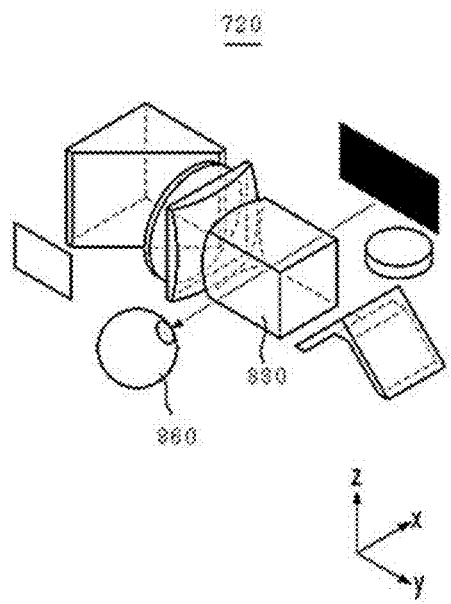
FIGS. 9A and 9B are views illustrating a path along which visible light comes to an augmented reality optical device from the outside according to the first embodiment.
Figure 9B:
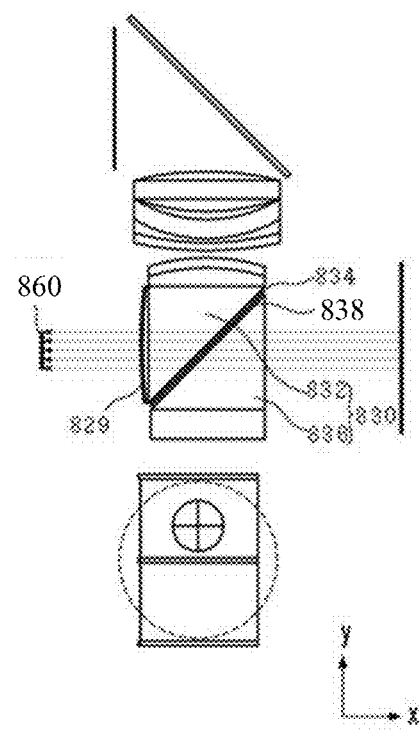

FIGS. 9A and 9B are views illustrating a path along which visible light comes to an augmented reality optical device from the outside according to the first embodiment.

Light corresponding to an actual image of an affected part, coming from the outside, is reflected by the affected part to the optical system 720. The light corresponding to the actual image of the affected part passes through the beam splitter 830 to the user's pupil 860. In this case, the light beams corresponding to the actual image of the affected part passes through the second reflection surface 838 of the beam splitter 830 and then some of the light beams are reflected by the first reflection surface 834 while others of the light beams are transmitted through the first reflection surface 834 to the user's pupil 860. Thus, the user may recognize the actual image of the affected part.

Since the patient may be in a high-illuminance space, if all of the light beams are incident onto the user's pupil 860 without a reduction in the amount of light, the user may experience glare. As the amount of light reduces while the light passes through the beam splitter 830, the optical system 720 may prevent glare.

Figure 10A:
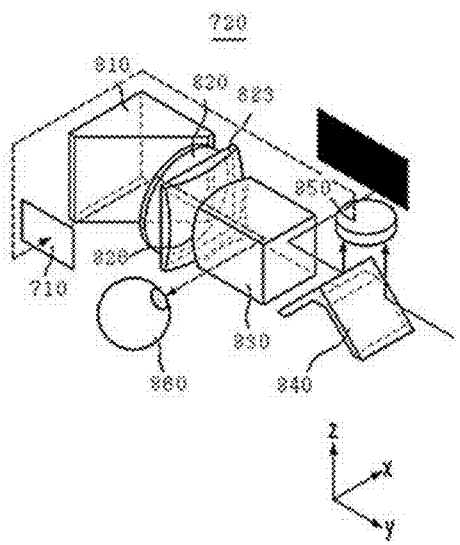
FIGS. 10A and 10B are views illustrating a path along which a preset wavelength range of light comes to an augmented reality optical device from the outside according to the first embodiment.
Figure 10B:
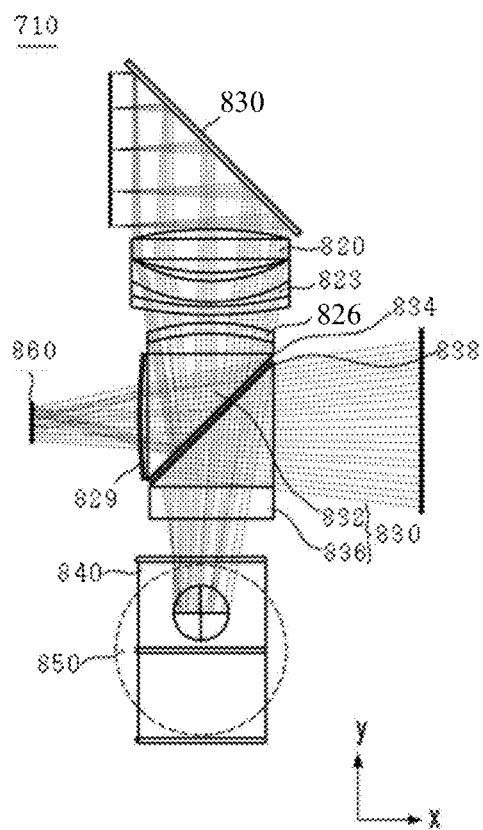

FIGS. 10A and 10B are views illustrating a path along which a preset wavelength range of light comes to an augmented reality optical device from the outside according to the first embodiment.

A preset wavelength range of light reflected by the affected part comes into the beam splitter 830 and all the light is reflected by the second reflection surface 838 to the second mirror unit 840. The preset wavelength range of light is re-reflected by the second mirror unit 840 to the image generator 850. The image generator 850 generates an affected part image and transfers the generated affected part image to the image output unit 710. The image output unit 710 outputs light corresponding to the affected part image, and the light is incident through the lens units 820, 823, 826, and 829 and the beam splitter 830 to the user's pupil 860. The light corresponding to the affected part image is incident onto the user's pupil 860 while being partially reflected by the first reflection surface 834.

Figure 11A:
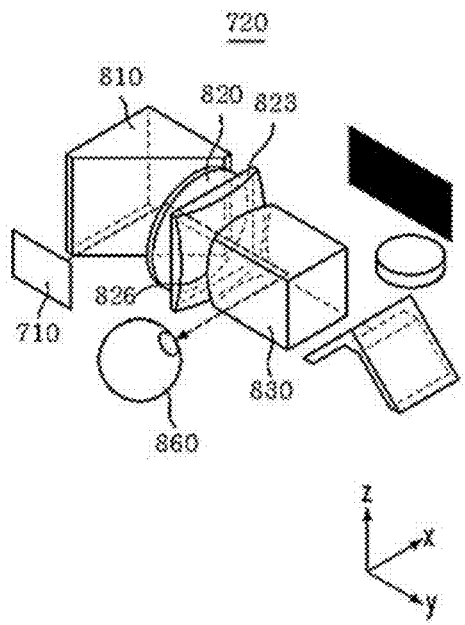
FIGS. 11A and 11B are views illustrating an optical path for an augmented reality optical device to output an augmented reality image according to the first embodiment.
Figure 11B:
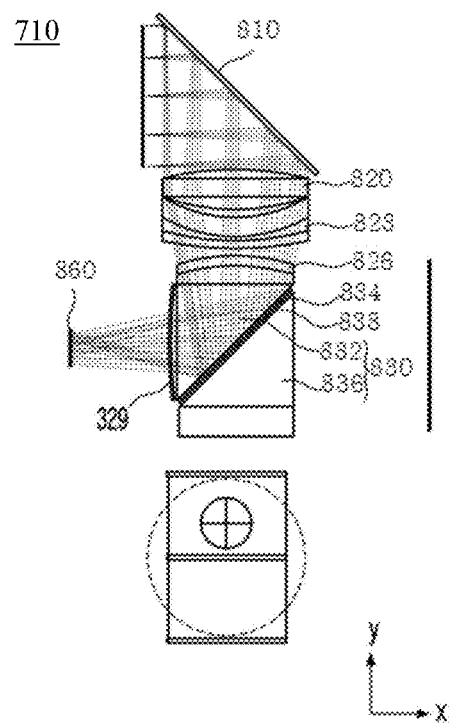

FIGS. 11A and 11B are views illustrating an optical path for an augmented reality optical device to output an augmented reality image according to the first embodiment.

The image output unit 710 receives the affected part information image from the outside and outputs light corresponding to the received affected part information image (e.g., an AR image). The light output from the image output unit 710 is incident through the lens units 820, 823, 826, and 829 and the beam splitter 830 to the user's pupil 860.

Thus, the user may simultaneously view the affected part image and the actual image of the affected part, and the user may additionally view the affected part information image.

Figure 12A:
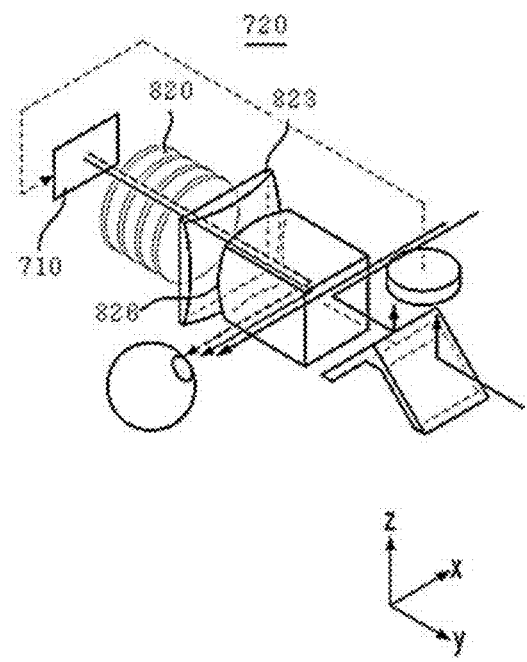
FIG. 12A is a perspective view illustrating an augmented reality optical device according to a second embodiment.
Figure 12B:
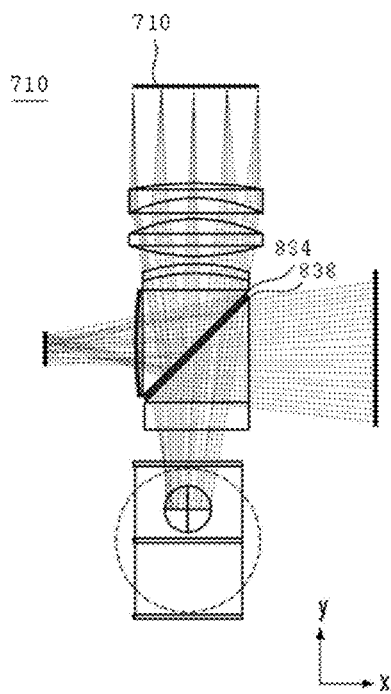
FIG. 12B is a plan view illustrating an augmented reality optical device according to the second embodiment.

FIG. 12A is a perspective view illustrating an augmented reality optical device according to a second embodiment. FIG. 12B is a plan view illustrating an augmented reality optical device according to the second embodiment.

Referring to FIGS. 12A and 12B, according to the second embodiment, an optical system 720 lacks the first mirror unit 810 that is a component of the optical system 720 of the first embodiment. According to the second embodiment, the image output unit 710 arranged along with the optical system 720 is disposed to face the lens units 820, 823, 826, and 829 to directly output light to the lens units 820, 823, 826, and 829. Thus, the augmented reality device 600 including the optical system 720 according to the second embodiment may relatively slim down.

Figure 13:
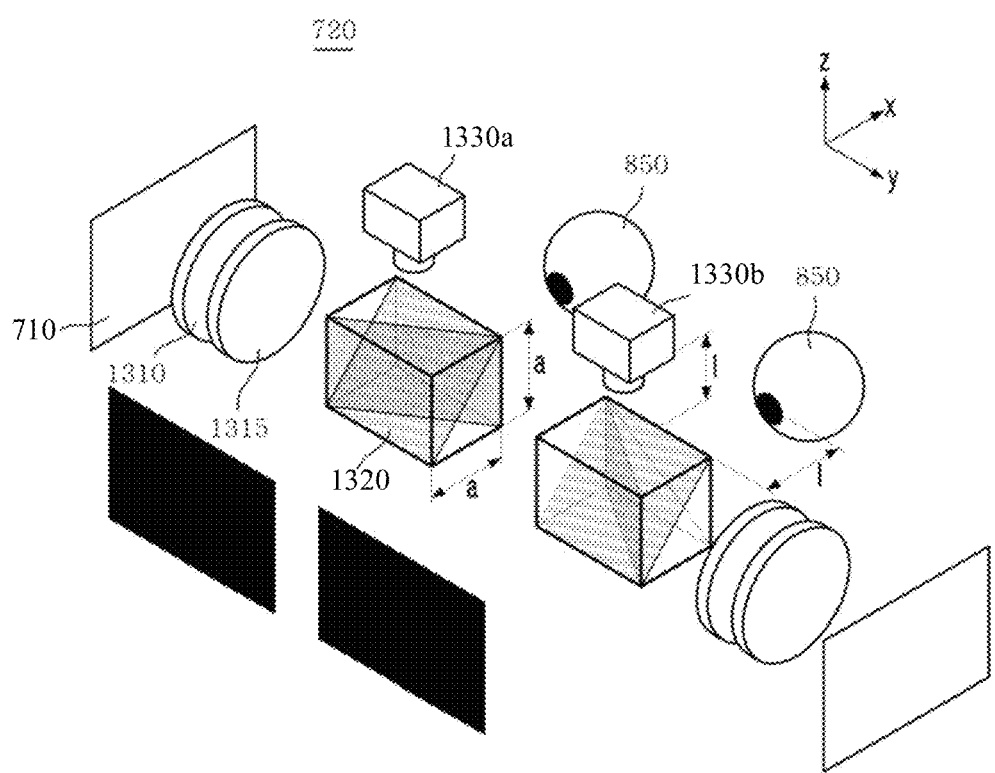
FIG. 13 is a perspective view illustrating an augmented reality optical device according to a third embodiment.

FIG. 13 is a perspective view illustrating an augmented reality optical device according to a third embodiment.

Referring to FIG. 13, according to the third embodiment, an optical system 720 includes lens units 1310 and 1315, a beam splitter 1320, and image generators 1330a and 1330b.

Like the lens units 820, 823, 826, and 829, the lens units 1310 and 1315 focus light output from the image output unit 710 and incident onto the user's pupil 860.

The beam splitter 1320 directly reflects all of light beams of a preset wavelength range, which come from the outside, to the image generators 1330a and 1330b, and the beam splitter 1320 reflects or transmits (a visible wavelength range of) light corresponding to the AR image output from the image output unit 710 or light corresponding to the actual image of the affected part coming from the outside. The beam splitter 1320 includes a plurality of reflection surfaces which are disposed in different directions to reflect the incident light beams in different directions. This is described below in greater detail. The user's pupil 860 and the image generators 1330a and 1330b are disposed in different directions with respect to the beam splitter 1320. The beam splitter 1320 reflects all of the preset wavelength range of light beams coming from the outside to the image generators 1330a and 1330b (e.g., the +z axis direction in the example of FIG. 13), and the beam splitter 1320 reflects or transmits a visible wavelength range of light beams output from the image output unit 710 or coming from the outside in the direction (e.g., the +x axis in the example of FIG. 13) where the user's pupil 860 is positioned and in other directions (e.g., the +y axis in the example of FIG. 13) where the user's pupil 860 and the image generators 1330a and 1330b are not positioned. As such, the beam splitter 1320 reflects incident light beams in different directions and, even without any additional component, allows light beams to be incident onto the image generator. Thus, the overall size or volume of the optical system 720 may reduce.

A length (a) of the beam splitter 830 in the direction along which light comes from the outside is identical to another length (a) of the beam splitter 830 in the direction towards the image generators 1330a and 1330b and perpendicular to the direction along which light comes from the outside. Thus, the length of the optical path where among the light beams coming from the outside, the visible wavelength range of light beams pass through the reflection surface and exit the beam splitter 1320 is identical to the length of the optical path where among the light beams coming from the outside, the preset wavelength range of light beams are reflected by the reflection surface and exit the beam splitter 1320.

The image generators 1330a and 1330b are positioned on one side of the beam splitter 830 and receive the preset wavelength range of light beams reflected by the beam splitter 830, thereby generating an affected part image. Unlike in the first and second embodiments, there are provided a plurality of image generators 1330 and 1330b to receive light beams reflected by the two beam splitters 1320, respectively, according to the third embodiment. The image generators 1330a and 1330b is spaced apart from each other by the user's inter-pupil distance.

The image generators 1330a and 1330b are spaced apart from the center of the beam splitter 1320 by the same distance as the distance I between the center of the beam splitter 1320 and the user's pupil 860. When the image generators 1330a and 1330b are so arranged, the following effects may be obtained. The length (a+I) of the optical path along which the preset wavelength range of light beams coming from the outside are incident through the beam splitter 1320 to the image generator 1330a and 1330b is identical to the length (a+I) of the optical path along which the visible wavelength range of light beams coming from the outside are incident through the beam splitter 1320 to the user's pupil 860. Since the image generators 1330a and 1330b are spaced apart from each other by the inter-pupil distance of the user, although the optical system has no separate component or post-treatment processing, the user may have an AOV and sense of depth as if he sees the real affected part, and the affected part image (e.g., AR image) generated by the image generators 1330a and 1330b and output to the user may represent the same depth as that of the actual affected part without distortion in depth. Since the image generators 1330a and 1330b receives light in the same environment as the user's pupil 860, the affected part image (AR image) causes no depth distortion.

Figure 14A:
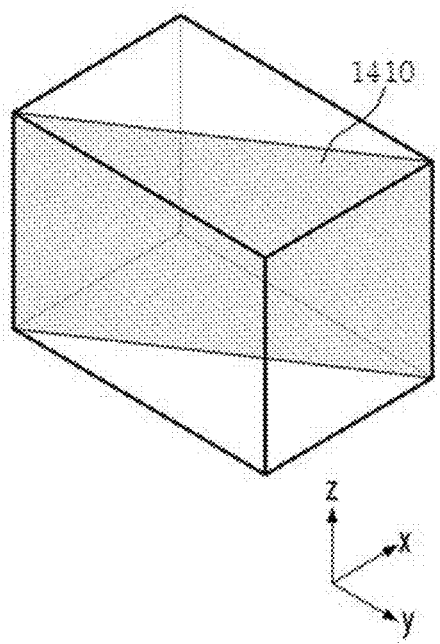
FIGS. 14A and 14B are views illustrating a reflection surface of a beam splitter in an augmented reality optical device according to the third embodiment.
Figure 14B:
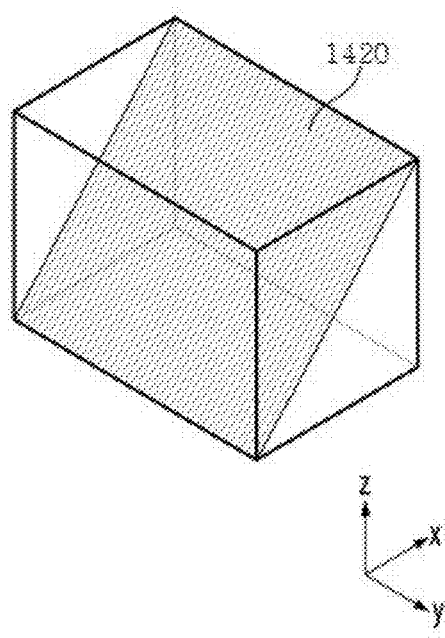
Figure 15A:
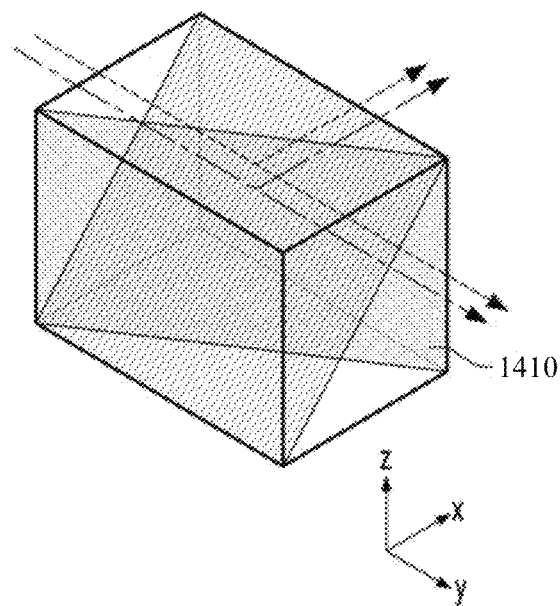
FIGS. 15A and 15B are views illustrating a beam splitter in an augmented reality optical device and an optical path of light incident onto a first reflection surface of the beam splitter according to the third embodiment.
Figure 15B:
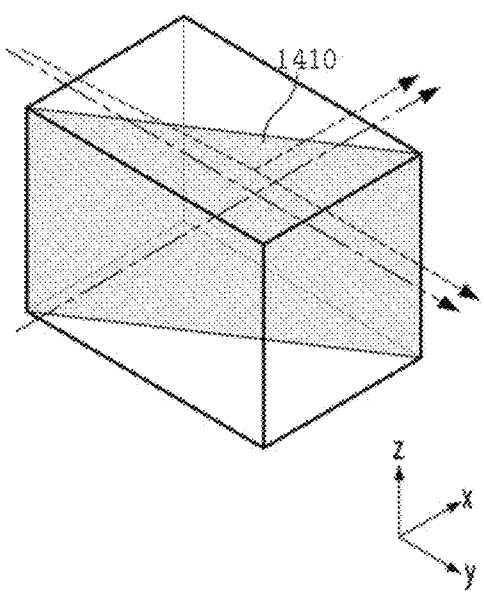
Figure 16A:
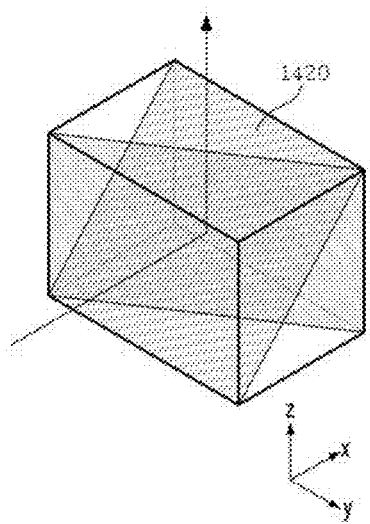
FIGS. 16A and 16B are views illustrating a beam splitter in an augmented reality optical device and an optical path of light incident onto a second reflection surface of the beam splitter according to the third embodiment.
Figure 16B:
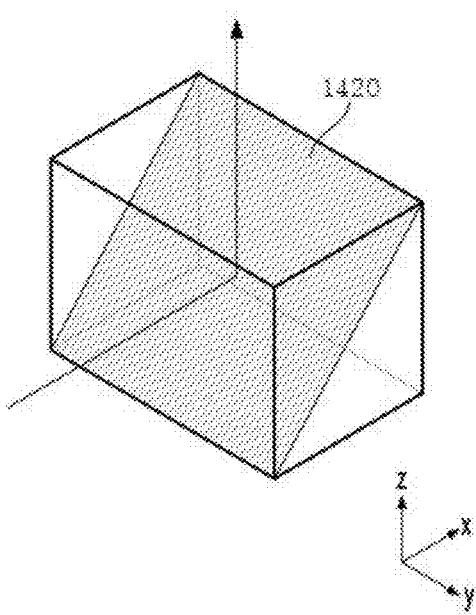

FIGS. 14A and 14B are views illustrating a reflection surface of a beam splitter in an augmented reality optical device according to the third embodiment. FIGS. 15A and 15B are views illustrating a beam splitter in an augmented reality optical device and an optical path of light incident onto a first reflection surface of the beam splitter according to the third embodiment. FIGS. 16A and 16B are views illustrating a beam splitter in an augmented reality optical device and an optical path of light incident onto a second reflection surface of the beam splitter according to the third embodiment.

The beam splitter 1320 includes a first reflection surface 1410 and a second reflection surface 1420 disposed in different directions to reflect incident light beams in different directions. The two reflection surfaces 1410 and 1420 are not separated from each other and are disposed in different directions. Thus, the two reflection surfaces 1410 and 1420 both are disposed in one beam splitter 1320.

The first reflection surface 1410 reflects some of the visible wavelength range of light beams coming from the outside or output from the image output unit 710 while transmitting others of the visible wavelength range of light beams. The first reflection surface 1410 transmits some of light beams coming from the outside to the user's pupil or reflects the others of the light beams in other directions (e.g., +y axis) along which the user's pupil and the image generators are not positioned. The first reflection surface 1410 reflects some of light beams output from the image output unit 710 to the user's pupil or transmits the others of the light beams in other directions (e.g., +y axis) along which the user's pupil and the image generators are not positioned.

The second reflection surface 1420 reflects all of a preset wavelength range of light beams, coming from the outside, while transmitting the other wavelength ranges of light beams. Thus, the preset wavelength range of light beams coming from the outside are all reflected by the second reflection surface 1420 to the image generators 1330*a* and 1330*b* while the light corresponding to the actual image of the affected part incident from the outside passes through the second reflection surface 1420.

The beam splitter 1320 including the first reflection surface 1410 and the second reflection surface 1420 may be manufactured as follows.

A raw material for the beam splitter 1320, which has no reflection surface, is cut into two parts in the direction of the first reflection surface or the second reflection surface.

The interfacial surface of each portion of the raw material is coated with a material according to the optical properties that the reflection surface of the cut direction needs to have.

After coating the interfacial surfaces with the material, the two portions are subjected to index matching bonding. The index matching bonding is performed with a material which has the same or similar refractive index to the material coated on the interfacial surface, thereby minimizing optical errors in the reflection surface.

Then, the resultant beam splitter which has the first reflection surface or the second reflection surface is cut into two portions in the direction of the other reflection surface.

The interfacial surface of each portion is coated with a material according to the optical properties that the cut reflection surface needs to have, and then, the two portions are subjected to index matching bonding, thereby forming the beam splitter 1320.

Thus, the beam splitter 1320 may have a plurality of reflection surfaces, and thus, its size or volume may be minimized. Since the beam splitter 1320 has the reflection surfaces in different directions, if the preset wavelength range of light beams are incident onto the beam splitter 1320, the light beams are all reflected by one of the reflection surfaces, which reflects all of the light beams while being prevented from coming through the other reflection surface to the user's pupil.

Figure 17:
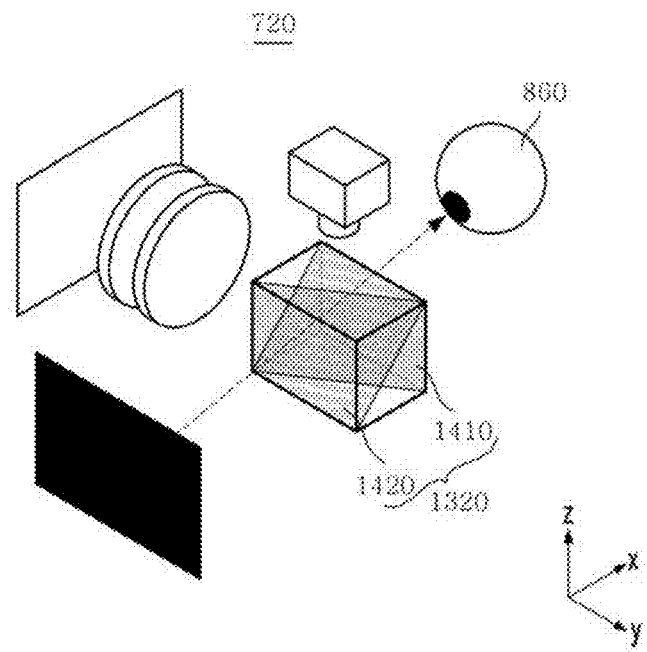
FIG. 17 is a view illustrating a path along which visible light comes to an augmented reality optical device from the outside according to the third embodiment.

FIG. 17 is a view illustrating a path along which visible light comes to an augmented reality optical device from the outside according to the third embodiment.

Light corresponding to an actual image of an affected part, coming from the outside, is reflected by the affected part to the optical system 720. The light corresponding to the actual image of the affected part passes through the beam splitter 1320 to the user's pupil 860. Thus, the user may recognize the actual image of the affected part.

Figure 18:
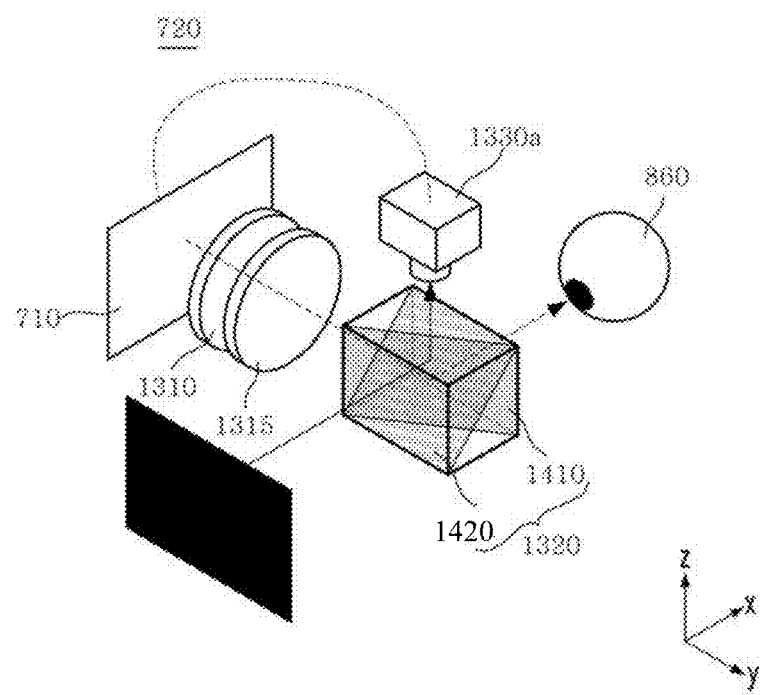
FIG. 18 is a view illustrating a path along which a preset wavelength range of light comes to an augmented reality optical device from the outside according to the third embodiment.

FIG. 18 is a view illustrating a path along which a preset wavelength range of light comes to an augmented reality optical device from the outside according to the third embodiment.

A preset wavelength range of light reflected by the affected part comes into the beam splitter 1320 and all the light is reflected by the second reflection surface 1420 to the image generator 1330*a*. The image generator 1330*a* generates an affected part image and transfers the generated affected part image to the image output unit 710. The image output unit 710 outputs light corresponding to the affected part image, and the light is incident through the lens units 1310 and 1315 and the beam splitter 1320 to the user's pupil 860. The light corresponding to the affected part image is incident onto the user's pupil 860 while being partially reflected by the first reflection surface 1410 of the beam splitter 1320.

Figure 19:
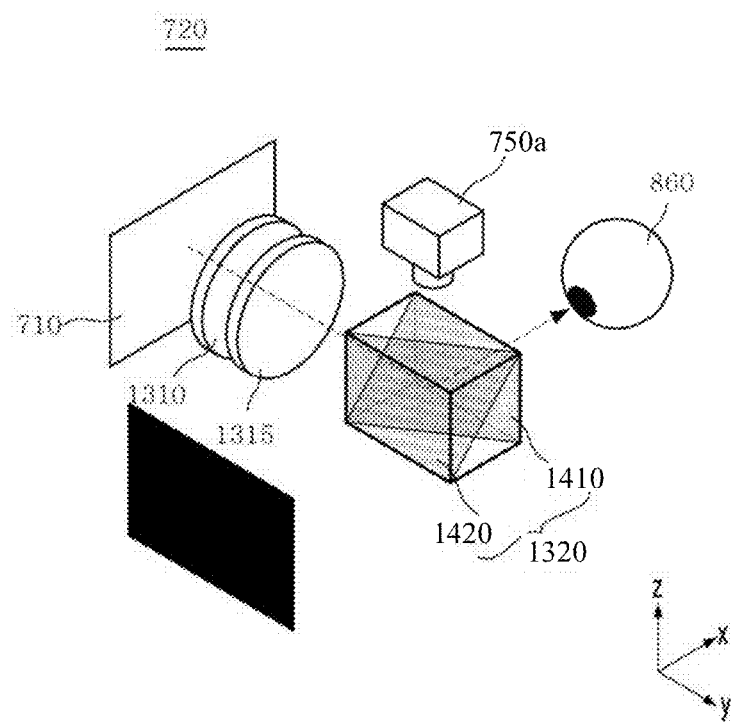
FIG. 19 is a view illustrating an optical path for an augmented reality optical device to output an augmented reality image according to the third embodiment.

FIG. 19 is a view illustrating an optical path for an augmented reality optical device to output an augmented reality image according to the third embodiment.

The image output unit 710 receives the affected part information image from the outside and outputs light corresponding to the received affected part information image (e.g., an AR image). The light output from the image output unit 710 is incident through the lens units 1310 and 1315 and the beam splitter 1320 to the user's pupil 860.

Thus, the optical system 720 of the third embodiment, although including only the lenses, beam splitter, and image generator, may advantageously output the actual image of the affected part and the AR image.

Figure 20A:
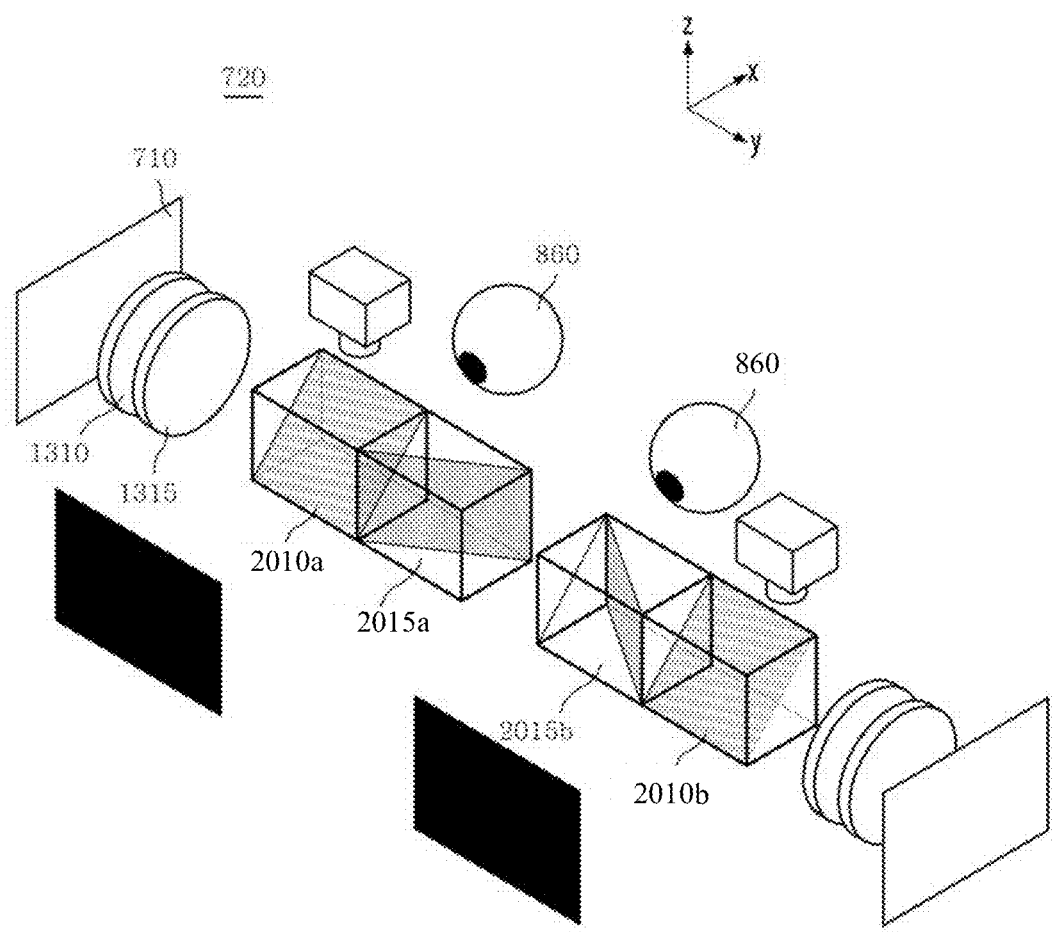
FIGS. 20A and 20B are perspective views illustrating an augmented reality optical device according to a fourth embodiment.
Figure 20B:
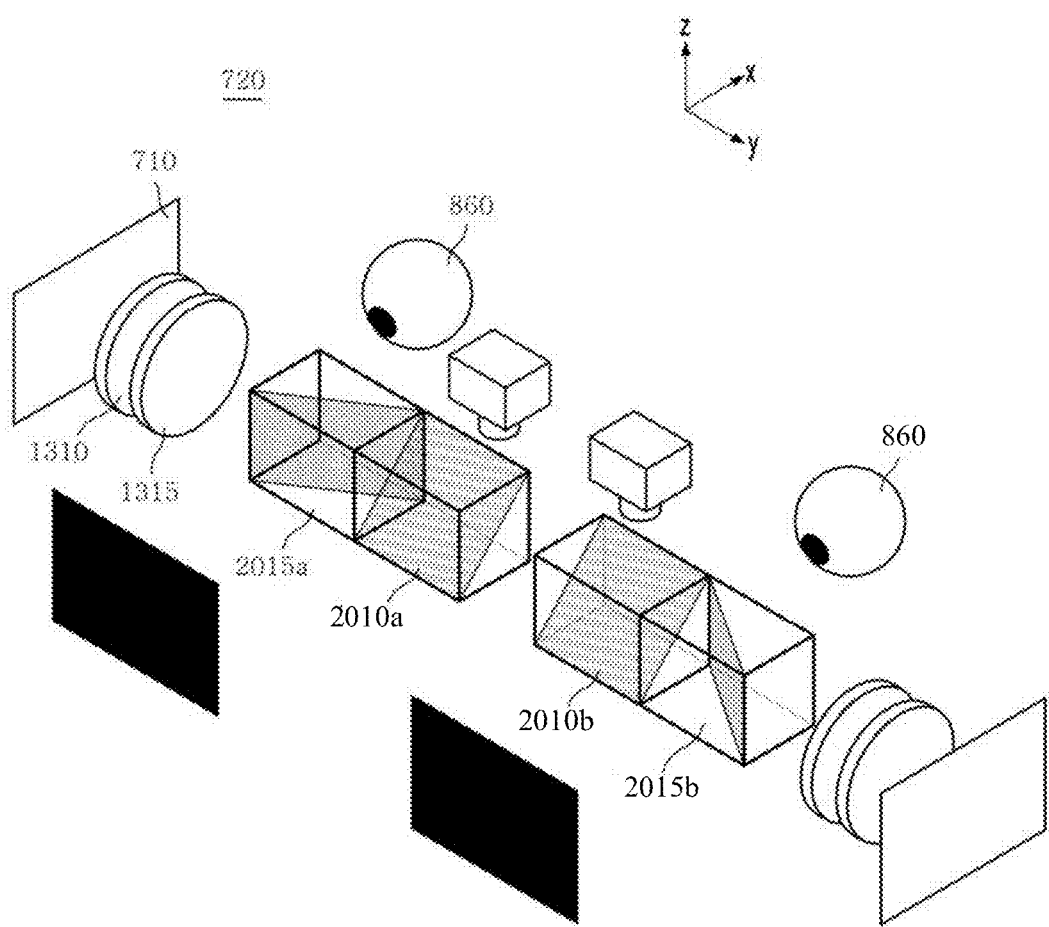

FIGS. 20A and 20B are perspective views illustrating an augmented reality optical device according to a fourth embodiment.

Referring to FIGS. 20A and 20B, according to the third embodiment, the augmented reality optical device 720 includes a first beam splitter 2010*a* or 2010*b* and a second beam splitter 2015*a* or 2015*b* instead of the beam splitter 1320. The first beam splitter 2010*a* or 2010*b* may be positioned relatively closer to the image output unit 710 than the second beam splitter 2015*a* or 2015*b* as shown in FIG. 20A or the first beam splitter 2010*a* or 2010*b* may be positioned relatively farther away from the image output unit 710 than the second beam splitter 2015*a* or 2015*b* as shown in FIG. 20B.

The first beam splitter 2010*a* or 2010*b* reflects all of a preset wavelength range of light beams coming from the outside (e.g., along the −x axis with respect to the beam splitters of FIG. 20) to the image generator. Unlike in the augmented reality optical device 720 of the third embodiment, the image generator is disposed in one direction (e.g., the +z axis in FIG. 20) with respect to the first beam splitter 2010*a* or 2010*b*, but the user's pupil 860 is not disposed on the axis of the first beam splitter 2010*a* or 2010*b*. Thus, the first beam splitter 2010*a* or 2010*b* reflects only the preset wavelength range of light beams in the direction along which the image generator is positioned.

The second beam splitter 2015*a* or 2015*b* reflects some of the visible wavelength range of light beams coming from the outside (e.g., −x axis with respect to the beam splitters of FIG. 20) and transmits others to the user's pupil 860. Unlike in the augmented reality optical device 720 of the third embodiment, the second beam splitter 2015*a* or 2015*b* is disposed on one side of the first beam splitter 2010*a* or 2010*b*, reflecting or transmitting the visible wavelength range of light beams.

The interval between the first beam splitters 2010*a* and 2010*b* may be identical to the interval between the image generators, and the interval between the second beam splitters 2015*a* and 2015*b* may be identical to the user's inter-pupil interval. The interval between the first beam splitters 2010*a* and 2010*b* or the interval between the second beam splitters 2015*a* and 2015*b* may be identical to the interval between the image generators, and the other interval may be identical to the user's inter-pupil interval. Thus, although the optical system has no additional component or post-treatment processing, the user may have an AOV and sense of depth as if he sees the target at the naked eye.

The augmented reality optical device 720 of the fourth embodiment includes separate beam splitters, e.g., a first beam splitter and a second beam splitter, to reflect or transmit a preset wavelength range of light beams and a visible wavelength range of light beams, respectively, and may thus be subject to an increase in size or volume as compared with the augmented reality optical device of the third embodiment. However, the augmented reality optical device of the fourth embodiment may be easily manufactured.

The above-described embodiments are merely examples, and it will be appreciated by one of ordinary skill in the art various changes may be made thereto without departing from the scope of the disclosure. Accordingly, the embodiments set forth herein are provided for illustrative purposes, but not to limit the scope of the disclosure, and should be appreciated that the scope of the disclosure is not limited by the embodiments. The scope of the disclosure should be construed by the following claims, and all technical spirits within equivalents thereof should be interpreted to belong to the scope of the disclosure.

What is claimed is:

1. An augmented reality optical device, comprising:
an image generator receiving a preset wavelength range of light reflected by an affected part and generating an image of the affected part, wherein the preset wavelength range is an infrared or ultraviolet wavelength range;
an image output unit outputting a visible wavelength range of light corresponding to the image generated by the image generator;
a lens unit focusing the light output from the image output unit; and
a beam splitter disposed under the image generator in a first direction of the augmented reality optical device, the beam splitter including a first surface and a second surface disposed in different directions to reflect incident light in different directions, the second surface reflecting the whole preset wavelength range of light to the image generator, and the first surface transmitting a first portion of the visible wavelength range of light and another visible wavelength range of light, incident from outside of the augmented reality optical device, to a pupil of a user positioned in a second direction of the augmented reality optical device, which is different from the first direction, while reflecting a second portion of the visible wavelength range of light and the other visible wavelength range of light in a preset direction other than towards the user's pupil and the image generator, or transmitting the first portion of the visible wavelength range of light and the other visible wavelength range of light in the preset direction while reflecting the second portion of the visible wavelength range of light and the other visible wavelength range of light to the user's pupil, wherein
a first length of the beam splitter in the first direction is identical to a second length of the beam splitter in the second direction perpendicular to the first direction, wherein
a distance between the image generator and a center of the beam splitter is identical to a distance between the center of the beam splitter and the user's pupil, and wherein the first surface and the second surface are positioned inside the beam splitter, and wherein the preset wavelength range is a wavelength other than the visible wavelength range.

2. The augmented reality optical device of claim 1, wherein the image output unit receives, from the outside, an AR image to be output and outputs another visible wavelength range of light corresponding to the AR image.

3. A medical augmented reality device, comprising:
an image generator receiving a preset wavelength range of light reflected by an affected part and generating an image of the affected part, wherein the preset wavelength range is an infrared or ultraviolet wavelength range;
an image output unit outputting a visible wavelength range of light corresponding to the image generated by the image generator;
an augmented reality optical device including a beam splitter disposed under the image generator in a first direction of the augmented reality optical device, the beam splitter including a first surface and a second surface disposed in different directions to reflect incident light in different directions, the second surface reflecting the whole preset wavelength range of light to the image generator, and the first surface transmitting a first portion of the visible wavelength range of light and another visible wavelength range of light, incident from outside of the augmented reality optical device, to a pupil of a user positioned in a second direction of the augmented reality optical device, which is different from the first direction, while reflecting a second portion of the visible wavelength range of light and the other visible wavelength range of light in a preset direction other than towards the user's pupil and the image generator, or transmitting the first portion of the visible wavelength range of light and the other visible wavelength range of light in the preset direction while reflecting the second portion of the visible wavelength range of light and the other visible wavelength range of light to the user's pupil;
a controller controlling the image generator, the image output unit, and the augmented reality optical device; and
a power supply supplying power to the image generator, the image output unit, the augmented reality optical device, and the controller, and wherein the first surface and the second surface are positioned inside the beam splitter.

4. An augmented reality optical device, comprising:
an image generator receiving first light of an infrared or ultraviolet wavelength range reflected by an affected part of a patient and generating an image of the affected part;
an image output unit outputting second light of a visible light wavelength range corresponding to the image;
a lens unit focusing the second light output from the image output unit; and
a beam splitter disposed under the image generator in a first direction of the augmented reality optical device,
wherein a first reflection surface and a second reflection surface are disposed, inside the beam splitter, to reflect incident light in different directions,
wherein the second reflection surface reflects the whole first light to the image generator, and
wherein the first reflection surface at least partially reflects the second light to a pupil of a user positioned in a second direction of the augmented reality optical device, which is different from the first direction, while at least partially transmitting third light of a visible light wavelength range, incident from outside of the augmented reality optical device, to the user's pupil.

* * * * *